United States Patent
Shih et al.

(10) Patent No.: US 9,423,534 B2
(45) Date of Patent: Aug. 23, 2016

(54) OPTICAL MODULE

(71) Applicant: Capella Microsystems (Taiwan), Inc., New Taipei (TW)

(72) Inventors: Cheng-Chung Shih, Fremont, CA (US); Yung-Chuan Chuang, Taipei (TW); Feng-Gang Shiue, Taipei (TW)

(73) Assignee: VISHAY CAPELLA MICROSYSTEMS (TAIWAN) LIMITED, New Taipei (TW)

( * ) Notice: Subject to any disclaimer, the term of this patent is extended or adjusted under 35 U.S.C. 154(b) by 64 days.

(21) Appl. No.: 14/484,756

(22) Filed: Sep. 12, 2014

(65) Prior Publication Data

US 2015/0369734 A1 Dec. 24, 2015

Related U.S. Application Data

(60) Provisional application No. 62/013,793, filed on Jun. 18, 2014.

(51) Int. Cl.
*G01N 21/55* (2014.01)
*G02B 5/00* (2006.01)

(52) U.S. Cl.
CPC .............. *G02B 5/003* (2013.01); *G01N 21/55* (2013.01); *G01N 2201/062* (2013.01); *G02B 5/005* (2013.01)

(58) Field of Classification Search
CPC . G01N 21/55; G01N 2201/062; G02B 5/005
USPC .................. 356/445–448, 450–458
See application file for complete search history.

(56) References Cited

U.S. PATENT DOCUMENTS

| | | | | |
|---|---|---|---|---|
| 3,851,221 A * | 11/1974 | Beaulieu | ................. | H01L 23/44 257/714 |
| 6,768,556 B1 * | 7/2004 | Matsumoto | ............ | B82Y 10/00 250/311 |
| 7,382,258 B2 * | 6/2008 | Oldham | .................. | B01L 3/545 340/572.1 |
| 7,508,505 B2 * | 3/2009 | Lustenberger | ..... | G01N 21/6408 250/208.1 |
| 7,616,315 B2 * | 11/2009 | Sharrock | .............. | G01N 21/274 356/436 |
| 7,674,638 B2 * | 3/2010 | Okudo | ................ | B81C 1/00269 257/48 |
| 7,675,624 B2 * | 3/2010 | Chinowsky | .......... | G01N 21/553 356/445 |
| 7,729,570 B2 * | 6/2010 | Yamada | ............. | G02B 6/12002 385/14 |
| 7,955,879 B2 * | 6/2011 | Kim | ...................... | H01L 33/507 257/98 |
| 8,616,067 B2 * | 12/2013 | Wagner | ................. | G01L 19/146 73/756 |
| 9,079,760 B2 * | 7/2015 | Goida | .................... | H04R 1/021 |
| 2014/0078507 A1 * | 3/2014 | Labrie | .................. | A61C 19/003 356/446 |
| 2014/0246337 A1 * | 9/2014 | Newman | .............. | A45C 11/005 206/5.1 |

\* cited by examiner

*Primary Examiner* — Tri Ton
*Assistant Examiner* — Jarreas C Underwood
(74) *Attorney, Agent, or Firm* — Muncy, Geissler, Olds & Lowe, P.C.

(57) ABSTRACT

An optical module is disclosed. The optical module includes: a package substrate; an optical device disposed on the package substrate; a clear mold disposed on the package substrate and the optical device; an light blocking mold disposed on the package substrate, surrounding an optical device on the package substrate, and having an opening above the optical device; and a flexible buffer layer disposed on the light blocking mold. The light blocking mold and the flexible buffer layer are integrally formed of light blocking materials different from each other. An optical module including a plurality of optical devices is also disclosed.

11 Claims, 8 Drawing Sheets

OPTICAL MODULE

CROSS-REFERENCE TO RELATED APPLICATION

This application claims the benefit of U.S. Provisional Application No. 62/013,793, filed on Jun. 18, 2014, in the United States Patent and Trademark Office, the disclosure of which is incorporated herein in its entirety by reference.

BACKGROUND OF THE INVENTION

1. Field of the Invention

The exemplary embodiment(s) of the present invention relates to an optical module. More specifically, the exemplary embodiment(s) of the present invention relates to an optical module with light blocking shield.

2. Description of Related Art

In recent years, with the development of personal mobile devices, various optical devices are incorporated in such personal mobile devices for different application. For example, the light sensor is often used in a smart phone or personal digital assistant (PDA) as a tool to detect object in motion such as a moving finger. To achieve the above effect, the optical sensor needs to receive light reflected by the target object. If there is no light block structure or member to define the angle of incident light for the optical sensor, the optical sensor may be susceptible to other light different from light reflected by the target object, and thus give incorrect detecting result. The more sensitive the optical sensor is, the more serious this problem may become. Similarly, the optical sensor can be used to detect the environmental luminance for displays with automatic brightness control function. If the light sensor receives the ambient light from the environment with the leaking light from the display, deviation may exist in the determination of environmental luminance and the brightness of the display may not be expected.

More particularly, please refer to FIG. 1 which is a schematic cross-section view of a current smart phone design. In FIG. 1, the optical device 20 comprises the aforementioned optical sensor and a die attached to the package substrate 10. (In the following, the optical device includes the die attached thereto) A clear mold 90 is disclosed on the optical device 20 and the package substrate 10 to protect the optical device 10 from damage due to environmental factors such as moisture or oxygen. The optical device 20, the package substrate 10 and the clear mold 90 form a packaged optical sensor as an optical module. The clear mold 90 may be made of transparent encapsulation material commonly used in this art, such as epoxy or silicone. The packaged optical sensor is soldered onto a printed circuit board (PCB) 50 and next to a liquid crystal display 40 enclosed by a case 41. A glass layer 30 and a light blocking member 31 are disposed on the optical device 20. Though the light blocking member 31 can block most ambient light, and the case 41 is opaque and can block most light from the LCD 40, there is still light leakage 1 from the LCD 40 through the gap between the light blocking member 31 and the case 41 and then passing through the clear mold 90. That is, the optical device 20 will rather be affected by light from the LCD 40 than only receive light through the glass layer 30 and the opening defined by the light blocking member 31 as desired.

To address the light leakage problem, some solutions have been provided. For example, please refer to FIG. 2 which is a schematic cross-section view of a smart phone design according to prior art. The difference between the structures in FIGS. 1 and 2 is that the package substrate 10, the clear mold 90, and the optical device 20 are surrounded by a rubber shield 60. Therefore, the light leakage through the gap between the light blocking member 31 and the case 41 is blocked by the rubber shield 60 and cannot reach the optical device 20. Moreover, the rubber shield 60 can be provided as a cushion between the rigid glass layer 30 and other structure, preventing the damage due to contact between the rigid glass layer 30 and other structure.

However, new problems arise from the structure shown in FIG. 2 in practice. Since the rubber shield 60 and other structures including the optical device 20, the clear mold 90, and the package substrate 10 are separately formed. An extra assembly process is required to set the rubber shield 60 to the desired position, such as on the clear mold 90 as shown in FIG. 2, which will increase the production cost. Besides, mismatch between assembling the rubber shield 60 and other structures may occur in the assembly process, so that the production yield may decrease. Assembly gaps may also exist between the light blocking member 31 and the rubber shield 60 due to the mismatch, so that the light leakage problem may not be completely solved by such means.

The information disclosed in the Background of the Invention section is provided only for better understanding of the background of the invention, and should not be taken as an acknowledgment or any form of suggestion that this information forms a prior art that would already be known to a person skilled in the art.

SUMMARY OF THE INVENTION

Therefore, it is a primary objective of the present invention to provide an optical module of preventing optical device being influenced by undesired light leakage and offering buffer function between the rigid outer layer such as glass layer and other structure without assembly process.

According to another aspect of the present invention, an optical module is provided. The optical module comprises: a package substrate; an optical device disposed on the package substrate; a clear mold disposed on the package substrate and the optical device; an light blocking mold disposed on the clear mold and the package substrate, surrounding the optical device and having an opening above the optical device; and a flexible buffer layer disposed on the light blocking mold. The light blocking mold and the flexible buffer layer are integrally formed of light blocking materials different from each other. The optical device may be a light sensor or a light transmitter.

Preferably, the flexible buffer layer may be black in color.

Preferably, the flexible buffer layer may be made of rubber.

According to another aspect of the present invention, an optical module is provided. The optical module comprises: a package substrate; a plurality of optical devices disposed on the package substrate; a plurality of clear molds disposed on the package substrate, and disposed on the plurality of optical devices, respectively; an light blocking mold disposed on the package substrate, surrounding the plurality of optical devices, and having openings above the plurality of optical devices, respectively; a flexible buffer layer disposed on the light blocking mold. The light blocking mold and the flexible buffer layer are integrally formed of light blocking materials different from each other, and the plurality of optical devices respectively disposed in different space formed by the light blocking mold with the corresponding clear molds. The functions of the plurality of optical devices can correspond to each other. The flexible buffer layer may be partially disposed on a top surface of the light blocking mold.

With the object, advantages, and features of the invention that may become hereinafter apparent, the nature of the invention may be more clearly understood by reference to the detailed description of the invention, the embodiments and to the several drawings herein.

BRIEF DESCRIPTION OF THE DRAWINGS

The exemplary embodiment(s) of the present invention will be understood more fully from the detailed description given below and from the accompanying drawings of various embodiments of the invention, which, however, should not be taken to limit the invention to the specific embodiments, but are for explanation and understanding only.

DETAILED DESCRIPTION OF THE PREFERRED EMBODIMENTS

Exemplary embodiments of the present invention are described herein in the context of optical modules.

Those of ordinary skilled in the art will realize that the following detailed description of the exemplary embodiment(s) is illustrative only and is not intended to be in any way limiting. Other embodiments will readily suggest themselves to such skilled persons having the benefit of this disclosure. Reference will now be made in detail to implementations of the exemplary embodiment(s) as throughout the drawings and the following detailed description to refer to the same or like parts.

Figure 3:
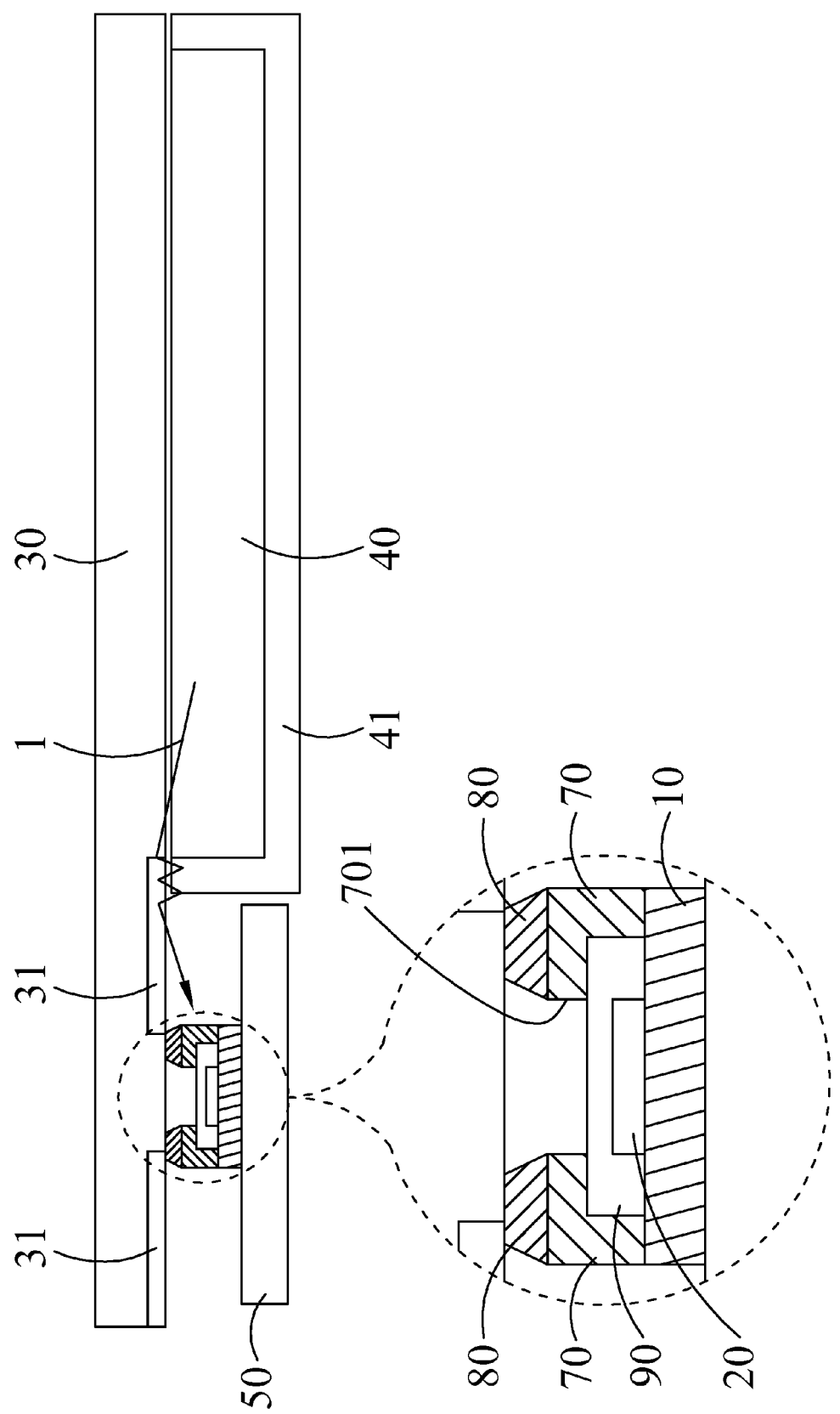
FIG. 3 is a schematic cross-section view illustrating a structure of a smart phone including a first embodiment of the optical module according to the present invention.

Please refer to FIG. 3 which is a schematic cross-section view illustrating a structure of a smart phone including a first embodiment of the optical module according to the present invention. As shown in the FIG. 3, the optical module according to the first embodiment of the present invention includes a package substrate 10; an optical device 20 disposed on the package; a clear mold 90 disposed on the package substrate 10 and the optical device 20; a light blocking mold 70 disposed on the package substrate 10 and the clear mold 90; surrounding the optical device 20, and having an opening 701 above the optical device 20; and a flexible buffer layer 80 disposed on the light blocking mold 70. The light blocking mold 70 and the flexible buffer layer 80 are integrally formed of light blocking materials different from each other.

Figure 1:
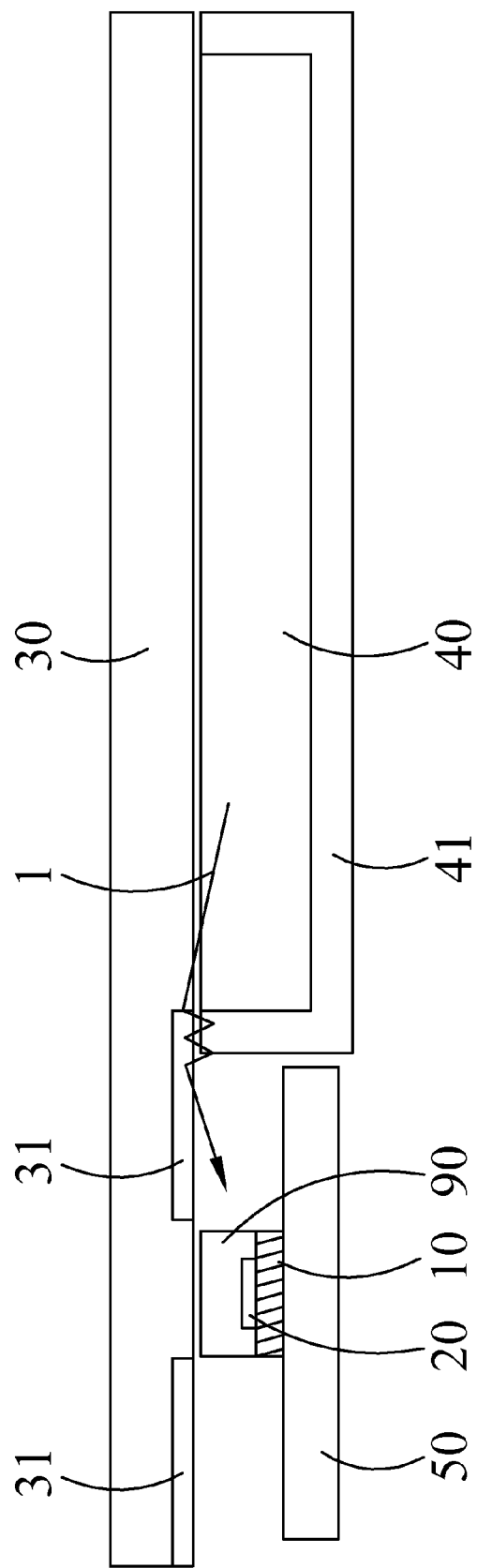
FIG. 1 is a schematic cross-section view illustrating a structure of a current smart phone.
Figure 2:
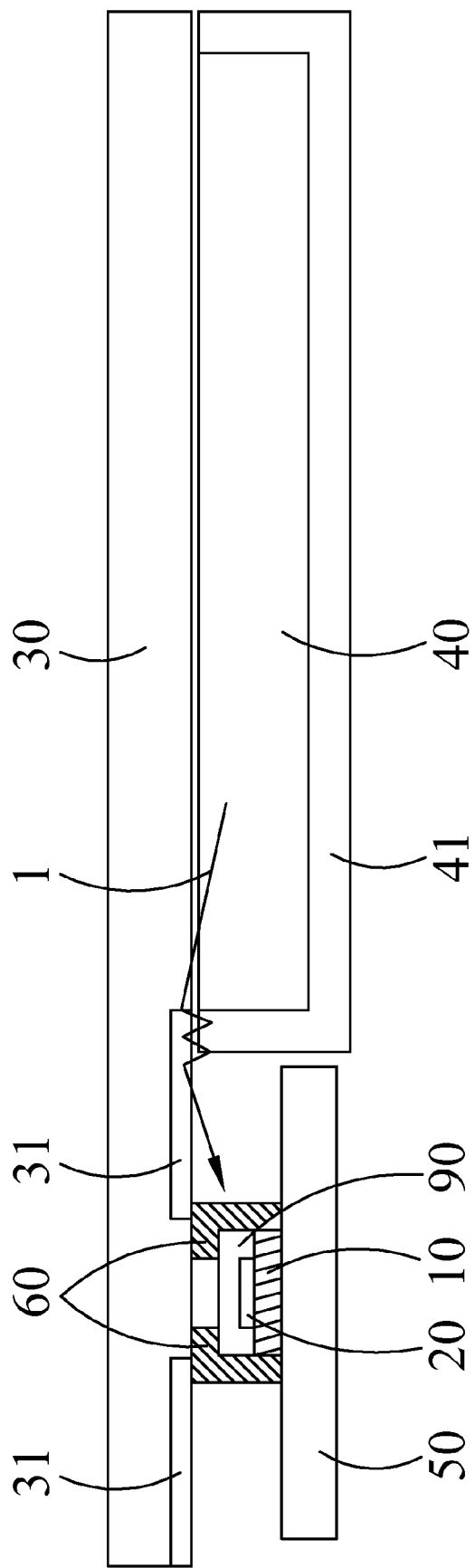
FIG. 2 is a schematic cross-section view illustrating a structure of a smart phone according to prior art.

The difference between the first embodiment of the present and the prior art shown in FIG. 2 is that the optical module of the first embodiment of the present invention include the light blocking mold 70 and the flexible buffer layer 80 instead of the rubber shield 60. Since the light blocking mold 70 is directly formed on the package substrate 10 and the clear mold 90, and the light blocking mold 70 and the flexible buffer layer 80 are integrally formed with each other, the flexible buffer layer 80 is disposed on the desired position without using assembly process. In the other words, the processes of manufacturing the light blocking mold 70, the flexible buffer layer 80 and/or the package substrate 10 can be compatible with each other, so the light blocking mold 70, the flexible buffer layer 80 and/or the package substrate 10 can be concurrently formed and thus the assembly process is not required. Moreover, the light blocking mold 70 and the flexible buffer layer 80 are made of light blocking materials to prevent the undesired light such as light leakage from the LCD 40 reaching the optical device 20, where the light blocking mold 70 can be made of hard material to provide supporting function and the flexible buffer layer 80 can be made of flexible material to provide buffering function. It is worth mentioning that the application of the optical module of the present invention is not limited thereto. For example, the optical module of the present invention can be used with various displays, such as organic light-emitting diode (OLED) display, electro-phoretic display (EPD), etc.

Preferably, the flexible buffer layer 80 may be black in color for light shield.

Since most of light from the LCD 40 (or other display) is visible light, the flexible buffer layer 80 may be black in color to effectively absorb the light leakage. However, the color of the flexible buffer layer 80 can vary depending on the type of the cooperative optical device 20 or the type of the neighboring light source.

Preferably, the flexible buffer layer 80 may be made of rubber.

To form the flexible buffer layer 80, rubber can be used. In the process of forming the flexible buffer layer 80, rubber in colloidal form can be disposed on the light blocking mold 70 during printing process such as screen printing and then be heated and cured. Therefore, the flexible buffer layer 80 can be firmly glued on the light blocking mold 70 and be shaped with flexibility as a cushion.

Figure 4:
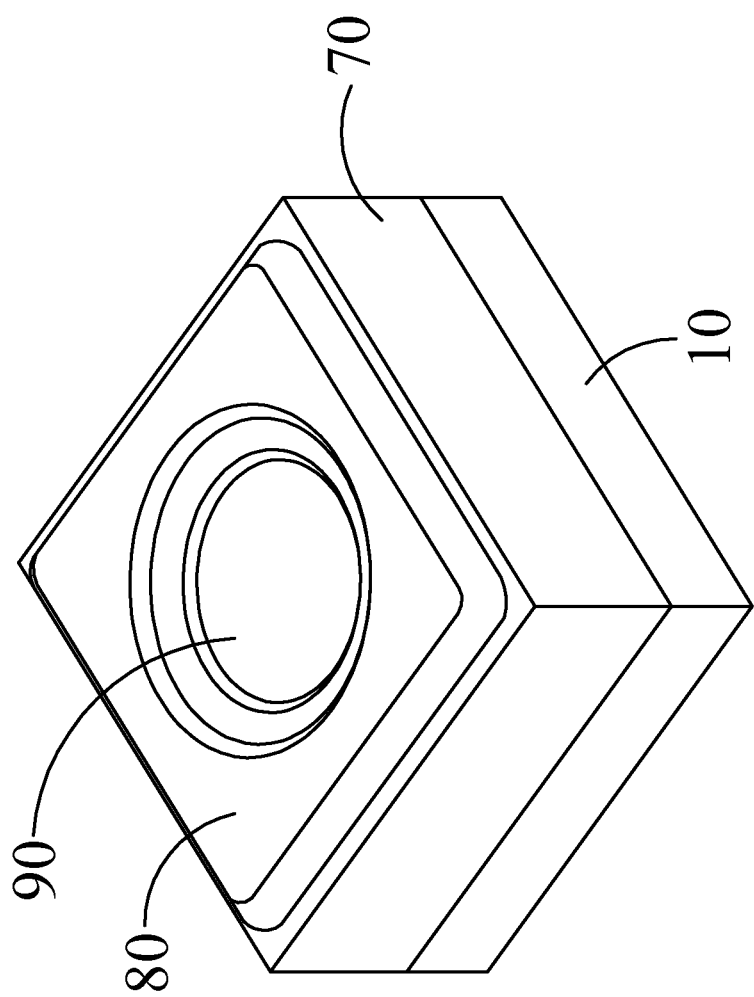
FIG. 4 is a schematic perspective view illustrating a second embodiment of the optical module according to the present invention.
Figure 5:
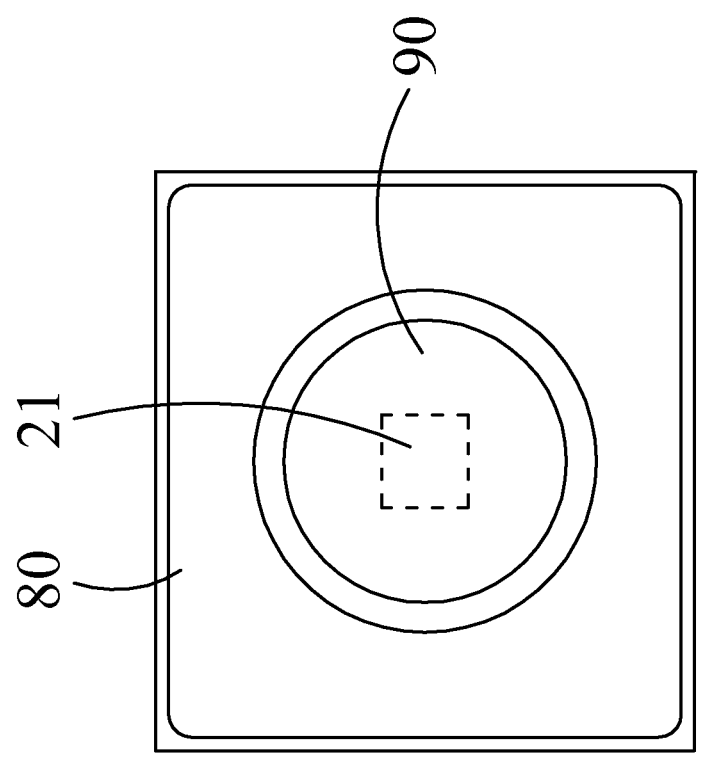
FIG. 5 is a schematic top view illustrating a second embodiment of the optical module according to the present invention.

Please refer to FIGS. 4 and 5 which are a schematic perspective view and a schematic top view illustrating a second embodiment of the optical module according to the present invention, respectively. In this embodiment, the optical device can be a light sensor 21 as shown in FIGS. 4 and 5. However, the present embodiment is not limited thereto, and for example, the optical device can be a light transmitter such as a light-emitting diode (LED).

Depending on the manufacturing process, the light sensor 21 can be formed with the package substrate 10, the clear mold 90, the light blocking mold 70 and the flexible buffer layer 80 as an optical module. The materials of the light blocking mold 70 and the flexible buffer layer 80 can be chosen corresponding to the light sensor 21. That is, light blocked by the light blocking mold 70 and the flexible buffer layer 80 can have the same wavelength as light the optical which can be detected by the light sensor 21. Since the light sensor 21, the package substrate 10, the light blocking mold 70 and the flexible buffer layer 80 can be integrally formed, the assembly process for the light sensor 21 is not required and thus the product yield may increase. Similarly, in the case the optical device is a light transmitter, the package substrate 10, the light blocking mold 70 and the flexible buffer layer 80 can be integrally formed as well, and the materials of the light blocking mold 70 and the flexible buffer layer 80 can be chosen corresponding to light emitted from the light transmitter. Therefore, light from the light transmitter may not undesirably affect neighboring optical devices, such as optical sensors. The formation of the light blocking mold 70 and the flexible buffer layer 80 of this embodiment is similar to that of the first embodiment, so the detailed description is omitted here.

Figure 6:
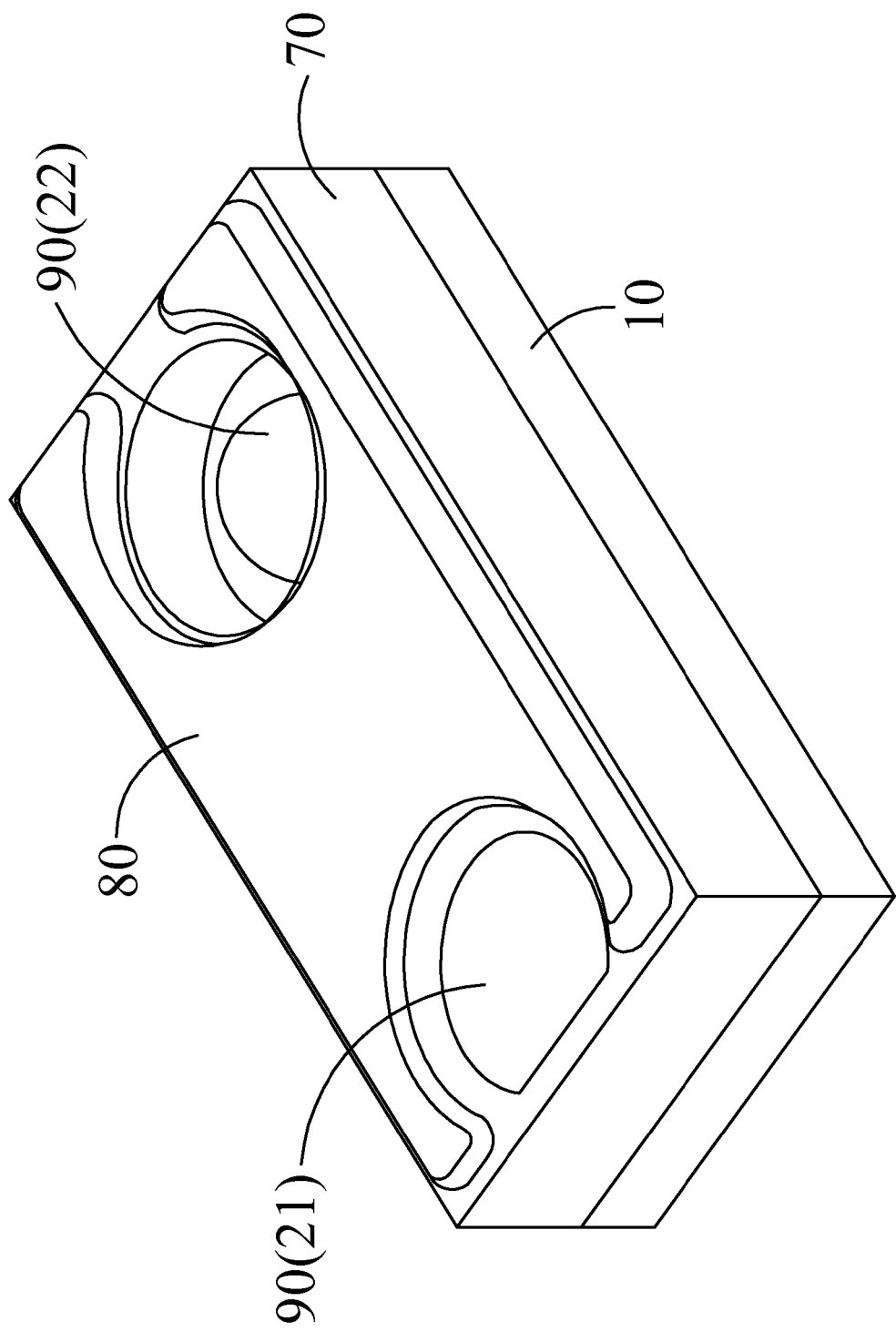
FIG. 6 is a schematic perspective view illustrating a third embodiment of the optical module according to the present invention.

Please refer to FIG. 6 which is a schematic perspective view illustrating a third embodiment of the optical module according to the present invention. The optical module of the third embodiment of the present invention comprises: a package substrate 10; a plurality of optical devices disposed on the package substrate 10; a plurality of clear molds 90 disposed on the package substrate, and disposed on the plurality of optical devices, respectively; an light blocking mold 70 disposed on the package substrate 10, surrounding the plurality of optical devices, and having openings above plurality of optical devices, respectively; a flexible buffer layer 80 disposed on the light blocking mold 70. The light blocking mold 70 and the flexible buffer layer 80 are integrally formed of light blocking materials different from each other, and the plurality of optical devices respectively disposed in different space formed by the light blocking mold 70 with the corresponding clear mold 90. In other words, the plurality of optical devices can avoid undesirable optical interference between each other by the light blocking mold 70 and the flexible buffer layer 80.

Moreover, the functions of the plurality of optical devices can correspond to each other. For example, the plurality of optical devices can include a light sensor 21 and a light transmitter 22 both enclosed by the clear molds 90 as shown in FIG. 6, and the light sensor 21 and the light transmitter 22 can cooperate with each other for motion sensing. For clarity, the shapes of the clear molds 90 are different from each other to show different optical devices (the light sensor 21 and the light transmitter 22) are enclosed in FIG. 6 (as well as FIGS. 7 and 8), but the present invention is not limited thereto. Specifically, the light transmitter 22 can emit light, the emitted light is reflected from a target, and the light sensor 21 receives the reflected light. Therefore, the optical module can detect the existence and motion of the target by repeating the above operations. Though only one light sensor 21 and one light transmitter 22 are shown in FIG. 6, but the present invention is not limited thereto. In some embodiments, the optical module of the present invention may include two or more light sensors and light transmitters for precise motion sensing function. The formation of the light blocking mold 70 and the flexible buffer layer 80 of this embodiment is similar to that of the first embodiment, so the detailed description is omitted here.

To sense motion with higher precision, the light leakage from the light transmitter 22 to the light sensor 21 must be reduced or prevented since the light leakage does not carry any information about the position of the target. Hence, as above discussed, the light blocking mold 70 and the flexible buffer layer 80 can reduce or prevent light emitted from the light transmitter 22 being received by the light sensor 21 without being reflected by the target. In addition, the plurality of optical devices such as the light blocking mold 70 and the flexible buffer layer 80 can be integrally formed with the package substrate 10, the light blocking mold 70 and the flexible buffer layer 80 and thus the production yield can increase and the production cost can decrease due to similar reasons discussed in above embodiments.

Figure 7:
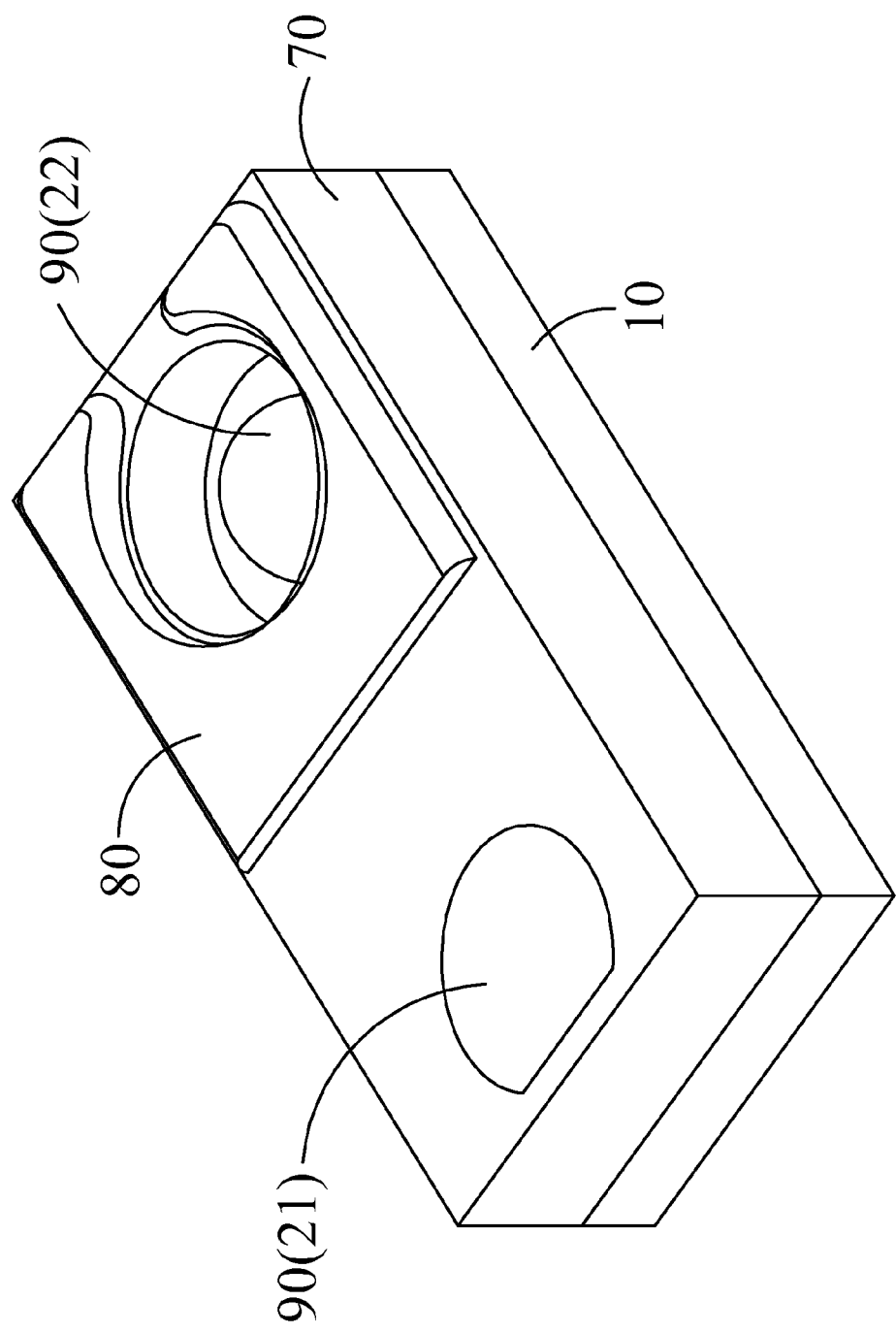
FIG. 7 is a schematic perspective view illustrating a forth embodiment of the optical module according to the present invention.
Figure 8:
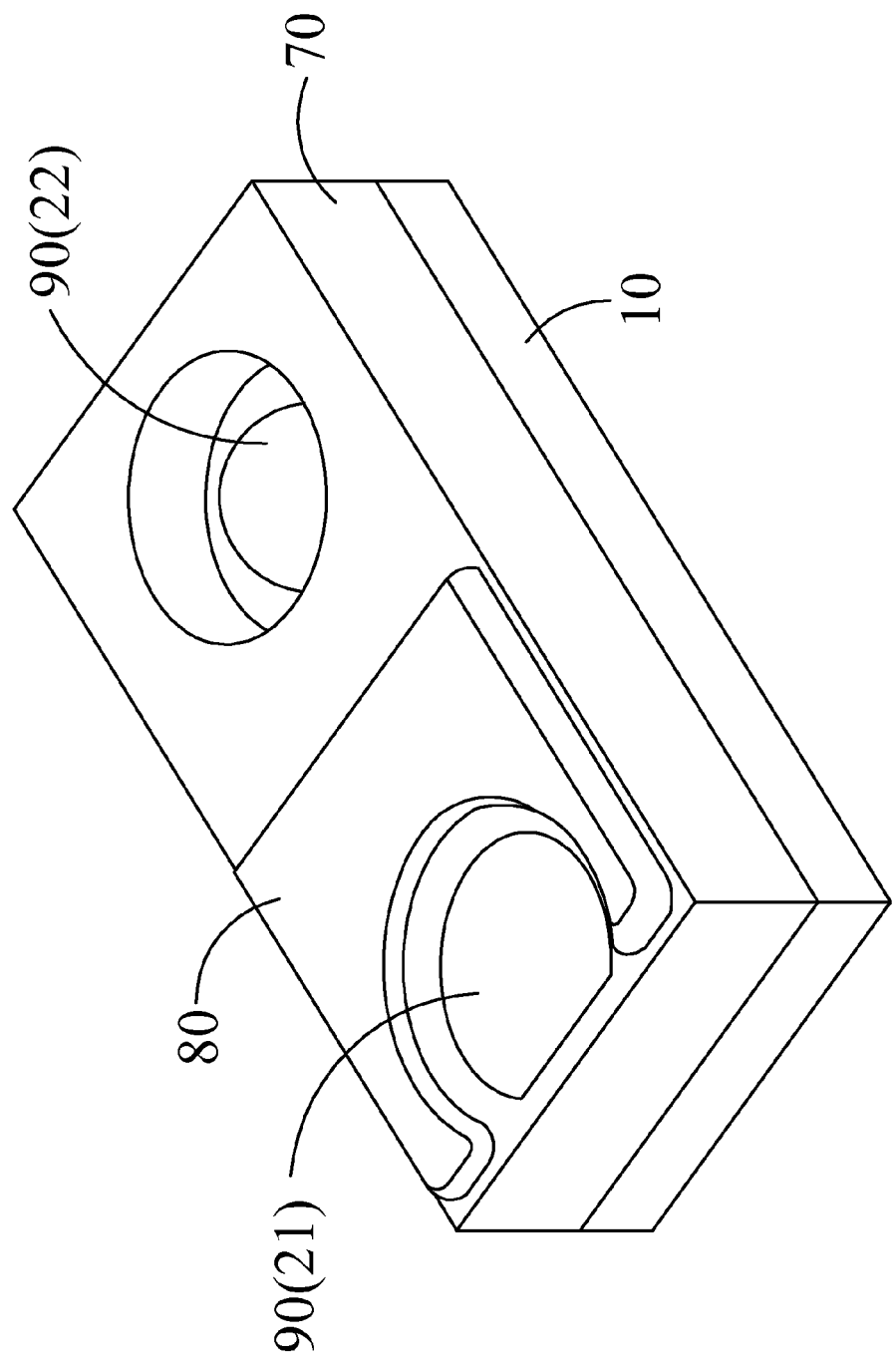
FIG. 8 is a schematic perspective view illustrating a fifth embodiment of the optical module according to the present invention.

Please refer to FIGS. 7 and 8 which are schematic perspective views illustrating a forth embodiment and a fifth embodiment of the optical module according to the present invention, respectively. As shown in FIGS. 7 and 8, the flexible buffer layer 80 can be partially disposed on a top surface of the light blocking mold 70.

To further save material of the flexible buffer layer 80 and reduce the volume of the optical module, the flexible buffer layer can be selectively disposed on some portions of the top surface of the light blocking mold. For example, the flexible buffer layer 80 may be mainly disposed at the position where the light leakage occurs most frequently or where the reason causing error of motion sensing is. Particularly, please refer to FIG. 7, if the light transmitter 22 in FIG. 7 is the main source of light leakage, then the flexible buffer layer 80 may only disposed at the position adjacent to the opening above the light transmitter 22. Alternatively, please refer to FIG. 8, if the light sensor 21 is highly sensitive and easily affected by the light leakage from the light transmitter 22, then the flexible buffer layer 80 may only disposed at the position adjacent to the opening above the light sensor 21. According to the size and the structure design of the optical module, the flexible buffer layer 80 may provide enough buffering function as a cushion without being disposed on the entire top surface of the light blocking mold 70. Therefore, the production cost of the optical module car further decrease.

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope of all such changes and modifications as are within the true spirit and scope of the exemplary embodiment(s) of the present invention.

What is claimed is:

1. An optical module, comprising:
    a package substrate;
    an optical device disposed on the package substrate;
    a clear mold disposed on the package substrate and the optical device;
    a light blocking mold disposed on the clear mold and the package substrate, surrounding the optical device, and having an opening above the optical device; and
    a flexible buffer layer disposed on the light blocking mold, wherein the light blocking mold and the flexible buffer layer are integrally formed of light blocking materials different from each other, and the light blocking mold is disposed between the flexible buffer layer and the clear mold.

2. The optical module as claimed in claim 1, wherein the flexible buffer layer is black in color.

3. The optical module as claimed in claim 1, wherein the flexible buffer layer is made of rubber.

4. The optical module as claimed in claim 1, wherein the optical device comprises a light sensor or a light transmitter.

5. An optical module, comprising:
    a package substrate;
    a plurality of optical devices disposed on the package substrate;
    a plurality of clear molds disposed on the package substrate and on the plurality of optical devices, respectively;

a light blocking mold disposed on the package substrate and the clear molds, surrounding the plurality of optical devices, and having openings above the plurality of optical devices, respectively;

a flexible buffer layer disposed on the light blocking mold, wherein the light blocking mold and the flexible buffer layer are integrally formed of light blocking materials different from each other, and the plurality of optical devices are respectively disposed in different spaces formed by the light blocking mold with the corresponding clear molds, and the light blocking mold is disposed between the flexible buffer layer and the clear mold.

6. The optical module as claimed in claim 5, wherein the flexible buffer layer is black in color.

7. The optical module as claimed in claim 5, wherein the flexible buffer layer is made of rubber.

8. The optical module as claimed in claim 5, wherein the flexible buffer layer is partially disposed on a top surface of the light blocking mold.

9. The optical module as claimed in claim 5, wherein the plurality of optical devices comprise a light sensor and a light transmitter.

10. The optical module as claimed in claim 9, wherein the flexible buffer layer is partially disposed on a top surface of the light blocking mold adjacent to the opening above the light sensor.

11. The optical module as claimed in claim 9, wherein the flexible buffer layer is partially disposed on a top surface of the light blocking mold adjacent to the opening above the light transmitter.

* * * * *